(12) United States Patent
DeSica et al.

(10) Patent No.: US 8,445,545 B2
(45) Date of Patent: May 21, 2013

(54) PHARMACEUTICAL COMPOSITION, METHOD OF PREPARATION AND METHODS OF TREATING ACHES/PAINS

(75) Inventors: Nicholas DeSica, Parkland, FL (US); Muhammed Ali, Fairfield, CA (US); Richard Li, Fairfield, CA (US)

(73) Assignee: Nicholas Desica, Parkland, FL (US)

( * ) Notice: Subject to any disclaimer, the term of this patent is extended or adjusted under 35 U.S.C. 154(b) by 463 days.

(21) Appl. No.: 12/437,370

(22) Filed: May 7, 2009

(65) Prior Publication Data

US 2009/0280184 A1    Nov. 12, 2009

Related U.S. Application Data

(60) Provisional application No. 61/051,090, filed on May 7, 2008.

(51) Int. Cl.
*A01N 25/00* (2006.01)
*A61K 47/00* (2006.01)
*A61K 9/14* (2006.01)

(52) U.S. Cl.
USPC ............... 514/784; 514/952; 424/489

(58) Field of Classification Search
USPC .................. 514/952, 784; 424/489
See application file for complete search history.

(56) References Cited

U.S. PATENT DOCUMENTS

| | | | |
|---|---|---|---|
| 4,684,666 A * | 8/1987 | Haas | 514/557 |
| 4,704,406 A * | 11/1987 | Stanislaus et al. | 514/570 |
| 5,110,606 A | 5/1992 | Geyer et al. | |
| 5,460,828 A | 10/1995 | Santus et al. | |
| 5,480,652 A | 1/1996 | Bru-Magntez et al. | |
| 5,780,046 A | 7/1998 | Humber et al. | |
| 5,901,591 A | 5/1999 | Kaplan | |
| 5,976,577 A | 11/1999 | Green et al. | |
| 6,068,999 A | 5/2000 | Hendrix | |
| 6,103,218 A | 8/2000 | Brucker et al. | |
| 6,312,736 B1 | 11/2001 | Kelly et al. | |
| 6,413,549 B2 | 7/2002 | Green et al. | |
| 6,767,925 B1 | 7/2004 | Deihl | |
| 6,770,263 B1 | 8/2004 | Brucker | |
| 6,793,934 B1 | 9/2004 | Burnside et al. | |
| 6,861,066 B2 | 3/2005 | Van de Casteele | |
| 2004/0048836 A1 | 3/2004 | Wilmott | |
| 2006/0141027 A1 | 6/2006 | Cioli | |
| 2006/0222722 A1 | 10/2006 | Roberts et al. | |

OTHER PUBLICATIONS

"Succussion", 2000, International Dictionary of Homeopathy.*

* cited by examiner

*Primary Examiner* — Gina C Justice
*Assistant Examiner* — Michael B Pallay
(74) *Attorney, Agent, or Firm* — Roylance, Abrams, Berdo & Goodman, L.L.P.

(57) ABSTRACT

Provided are methods and compositions useful for treating/ aches and/or pains. The compositions comprise an herbal therapeutic agent and an analgesic agent, wherein the composition is effective when delivered to the mucosal membrane.

10 Claims, No Drawings

PHARMACEUTICAL COMPOSITION, METHOD OF PREPARATION AND METHODS OF TREATING ACHES/PAINS

CROSS-REFERENCE TO RELATED APPLICATION

This application claims the benefit of Provisional Application No. 61/051,090, filed May 7, 2008.

FIELD OF THE INVENTION

The present invention relates to a pharmaceutical composition containing (a) herbal therapeutic agents that include feverfew and ginger each having an average particle size of about 0.01 to 500 nm and (b) an analgesic preparation comprising ibuprofen having an average particle size of about 0.01 to 500 nm. The invention also contemplates a method of administering the sublingual spray pharmaceutical composition to a patient for the treatment of aches, pains and/or inflammation in muscles, joints and/or tissues as well as a method for preparing the composition.

BACKGROUND OF THE INVENTION

Aches, pains, and discomfort are common problems. For example, ibuprofen has the chemical name 2-(4-Isobutylphenyl)propionic acid and is a well-tolerated drug possessing analgesic, antipyretic and anti-inflammatory activities (Merck Index, 11th edition, no. 4812). Current treatments for such pains are pills, gelatin capsules, and powder capsules that make their way through the gastrointestinal tract to the circulatory system. Such a traversal of the various organs in the body depletes the active ingredients in the liver, stomach and intestines while exposing the tissues of those organs to the effects of the active ingredient. Some patients have experienced stomach irritation and ulcers from orally ingested treatments. Some adults and many young children also have difficulty swallowing such pills and actively seek other forms of such medication. Other ways to administer analgesic medications and treatments include subcutaneous injections and nasal sprays. Subcutaneous injections are painful and difficult to self-administer. Nasal sprays have hitherto experienced stability problems with the dispersion and integrity of the active ingredients.

A number of analgesic and therapeutic medications and homeopathic treatments are known and reflected in one or more patents. The interest in homeopathic and/or herbal medicines has increased recently due in part to the lower cytotoxicity associated with such medications. Homeopathy is commonly used to mean a system of medicine based on the use of infinitesimal doses of medicines capable of producing symptoms similar to those of the disease treated. By stimulating a subject's natural defenses (i.e., increasing the symptoms) the subject will be motivated or directed towards homeostasis, since one's symptoms are actually efforts of the organism to reestablish homeostasis or balance. Homeopathic treatment encompasses some forms of natural materials including plant extracts and the like. However, some natural plant extracts are not necessarily homeopathic treatments as the extracts themselves do not stimulate disease or disorder symptoms but rather inhibit their onset or severity.

For example, ginger has been used with some success for relief of nausea. The administration of 1,000 to 2,000 mg of ginger orally by tablet has been found to effectively reduce nausea in the case of motion sickness.

Another example is feverfew, an herb that is widely available and has been investigated in modem times. Historically, feverfew is known to have been used in the treatment of fevers, from whence it derives its name, and also in rheumatic conditions. Fresh feverfew leaves have sometimes been chewed by subjects wishing to rid themselves of migraine. However, a common adverse effect reported by those who have used this technique is the generation sores in the mouth and sensitization of oral tissues. Additionally, many patients find this mode of administration to be crude and unpleasant. Feverfew tablets or capsules do not expose the mouth tissues to the same effects as chewed leaves and have been employed by practitioners of herbal medicine.

The use of feverfew for treatment of migraines is known. For example, U.S. Pat. No. 6,103,218 to Brucker, et al. discloses a composition and delivery system in which feverfew is delivered in the form of an aqueous nasal spray for the relief of migraine headaches.

The use of a combination of feverfew and ginger for the treatment migraines in a sublingual form is known. U.S. Patent Application Publication No. 2006/0222722 to Roberts, et al. discloses sublingual methods of treating arthritis by administering a composition including feverfew and ginger. The reference lacks disclosure of combining ibuprofen in the composition and moreover, the ability to make a stable, sublingual pharmaceutical spray composition in which an ingredient of the composition is a stable, water-soluble ibuprofen.

The combination of analgesics and feverfew dissolved in aqueous mediums for treating aches and/or pains has also been suggested. U.S. Pat. No. 6,770,263 to Brucker discloses a composition that comprises an aqueous medium in which feverfew and an analgesic are dissolved or dispersed. One problem associated with such a composition is that the analgesic, such as ibuprofen, is not stable for extended periods and through a wide variety of temperature extremes.

Liquid formulations for delivering medicaments and herbal therapeutic agents is not, however, a new development. Biologically active agents such as nutritional supplements, hormones, and a variety of pharmaceutical preparations are typically provided in oral (liquids or solids) or injectable dosage formulations. There are, however, difficulties with maintaining stability of the solution or dispersion without precipitation and with maintaining efficacy of the ingredients associated with this formulation.

One manner to overcome the limitations discussed above is to produce granulates from powder mixtures. For purposes of administration, these granulates are usually converted into tablets, enclosed in capsules or in sachets. It has also been long known that granules or tablets can be coated with films, which can serve to delay the release of the active ingredient they contain, disguise an unpleasant taste, and/or improve the stability of the composition. A major limitation of the use of such coated granulates in liquid formulations is that it has been difficult to obtain particles of an appropriate size to enable them to be easily suspended and kept in suspension in the fluid vehicle.

One manner of producing granules involves the use of a conventional mixer-granulator, which consists of a vessel, which may be of varying shape, equipped with an agitator that keeps the powder moving while the granulation fluid is being added. The motion is slow and the resulting globules, even though suitable for making conventional dosage forms such as tablets or capsules, does not possess the density, shape and particle-size distribution suitable for subsequent coating.

Unlike conventional mixer-granulators, extruder-spheronizers can produce spherical particles of homogeneous sizes and even shapes and surfaces. The limitation that prevents their application to microgranulates suitable for liquid suspensions is the average product size, which is rarely smaller than 1-2 mm and in any case never smaller than 500 μm.

It would be desirable to have a method for producing analgesic and similar pain-treating compositions that could produce particles of very fine size in a stable, aqueous formulation.

It would also be desirable to have a spray formulation that would require low concentrations of active ingredients for contact with sublingual mucosal tissues.

SUMMARY OF THE INVENTION

It is an objective of the invention to provide a process for making a composition having a super-fine particle size that can form a stable aqueous dispersion and/or solution.

In accordance with this and other objectives of the invention that will become apparent from the description herein, the present invention provides a composition having dispersed or dissolved therein (a) an analgesic preparation including ibuprofen and (b) an herbal therapeutic agent comprising a mixture of feverfew and ginger, wherein the average particle size of the analgesic preparation and the herbal therapeutic agents is about 0.01 to 500 nm.

The invention also provides a method of treating a subject disposed to aches, pains and/or tissue inflammation including headache, migraine, toothache, earache, joint pain, backache, abdominal cramps, and the like comprising administering an effective amount of the composition described above, wherein relief from the pain and/or tissue inflammation occurs within minutes of the administering.

As described more fully herein, the invention also provides a method of forming a stable, water-soluble composition suitable for sublingual, buccal, or via the gastrointestinal tract—administration that includes the steps of: (a) dissolving ibuprofen USP grade powder, preferably with a dissolution solution that includes water, alcohol, glycerin or a combination thereof to form a dissolved ibuprofen solution; (b) transferring said dissolved ibuprofen solution to a vacuum equipped vessel having a high shear mixer mounted thereon; and (c) mixing said dissolved ibuprofen solution with said high shear mixer for a time sufficient to reduce the average particle size of said dissolved ibuprofen to less than or equal to 500 nanometers. Preferably, the process also contemplates (d) allowing the mixture from step c) to rest for 10-20 minutes and (e) equilibrating the product for approximately 24 hours.

Also contemplated herein is a method of treating a subject disposed to a disorder having symptoms that include aches, pains and/or tissue inflammation is described that includes: administering to a subject via sublingual, buccal, or the gastrointestinal tract, an effective amount of a spray composition comprising an analgesic such as ibuprofen, feverfew, and ginger having an average particle size of about 500 nanometers or less.

The invention further provides a method of producing a sublingual spray composition comprising therein an analgesic such as, for example, ibuprofen, feverfew and ginger, wherein the sublingual spray is tolerant to mucus membranes.

In a preferred aspect of the present invention, a composition according to the invention comprises ibuprofen, feverfew extract and ginger extract each having an average particle size of less than about 500 nm in an aqueous spray formulation. In this embodiment, the spray comprises ibuprofen, feverfew extract and ginger extract, as well as other ingredients in the formulation to provide a spray suitable for administration of the composition of ibuprofen, feverfew extract and ginger extract sublingually.

The present invention provides a commercially viable method for making a highly effective, stable analgesic composition that can be administered via sublingual, buccal, or the gastrointestinal tract. The composition is stable through a variety of conditions and permits administration of effective pain and/or inflammation treatments to a wide variety of patients under even the most adverse and unsanitary circumstances.

The mucosal tissue does not contain the acids and enzymes present in the gastrointestinal tract. Thus, via the sublingual route, the herbal medicines disclosed herein, as well as the analgesic, are readily available for absorption into the blood stream and related tissues of the subject without unwanted degradation. Accordingly, smaller amounts of such herbal medicines and/or analgesics are useful in order to treat a subject afflicted with a disease or disorder causing aches, pains, and/or discomfort. The smaller amounts used in the compositions and methods of the invention also result in less gastrointestinal discomfort, sores, and the like.

In addition, administration to the mucus membrane results in a faster uptake of the medicinal product and/or active ingredient. Accordingly, any ache, pain, and/or discomfort will not reach the same severity as with gastrointestinal routes of administration due to the rapid uptake of the compositions.

DETAILED DESCRIPTION OF THE INVENTION

The present invention provides methods and compositions that utilize small amounts of herbal medicines along with an analgesic, ibuprofen in a formulation, such as a spray formulation, characterized by dispersed particles having an average diameter of about 500 nm or less. The invention provides compositions for administration to a subject including, for example, via sublingual, buccal, or the gastrointestinal tract.

Ingredients

The present composition also contains ibuprofen. Ibuprofen is a non-steroidal anti-inflammatory agent (NSAID) which is known to possess analgesic and antipyretic activities. It is useful in the treatment of pain and inflammation associated with various maladies, including the common cold, toothaches, headaches, backaches, menstrual cramps (Dysmennorhea), the muscular aches and pains associated with Premenstrual Syndrome, rheumatoid arthritis and osteoarthritis, as well as in the reduction of fever.

Feverfew extract is derived from the feverfew plant (*Tanaecetum parthenium*), which is also known, for example, as *Chrysanthemum parthenium, Chrisanthemum parthenium, Pyrethrum parthenium, Tanacete parthenii herba* or *folium, Matricaria parthenoides, Matricaria parthenium, Leucanthemum parthenium, Matricaria parthenium,* Spanish pellitory, Featherfew, Featherfoil, feather-fully, and by a number of common names, various of which are used throughout the world (Midsummer daisy, Bachelor's buttons, Altamisa, nosebleed, flirtwort, ague plant, devil daisy, feddygen fenyw (Welsh), maid's weed, Missouri snakeroot, mutterkaut (German), prairie-dock, vetter-voo, wild chamomile, grande camomille (French), Santa Maria (Spain), febrifuge plant.) The extract may be obtained by techniques known in the art using solvents such as petroleum spirits or polar organic solvents. See U.S. Pat. No. 5,384,121 to Rhodes, and also WO 94 06800; EP 0 553 658; WO 92 11857; GB 2,166, 952; EP 98 041; WO 98 39018. The disclosures of these patents are herein incorporated by reference.

The extract of the feverfew plant at least initially contains parthenolide, and may additionally contain other components such as Polyynes, Flavonoids and Volatile oils including camphor, borneol and others. Feverfew also contains relatively large quantities of sesquiterpene lactones, primarily parthenolide.

In addition to parthenolide, feverfew is known to contain the following non-ubiquitous chemicals: 1-Beta-hydroxyarbusculin, 10-Epicanin, 8-Beta-reynosin, Apigenin-7-glucoside, Chrysanthemolide, Chrysanthemonin, Chrysartemin-A, Chrysartemin-B, Cosmosiin, L-Borneol, L-camphor, Mangoliolide, Reynosin, Santamarin, Tanaparthin, Tanaparthin-1-alpha, 4-alpha-epoxide, Tanaparthin-1-beta, 4-beta-epoxide, tenetin 3-b-hydroxyparthenolide, seco-tanaparthenolide A, canin, artecanin, and balchanin.

Because feverfew extract may contain additional beneficial components, compositions comprising the extract of feverfew are generally preferred for use in the present invention as compared to compositions comprising a highly purified parthenolide that has been isolated from the additional components naturally occurring in feverfew extract.

Feverfew (Tanacetum parthenium) is an herb in the Compositae family that has been known to have therapeutic properties with mode of action based on inhibiting the release of the vasoconstrictor serotonin from platelets. Accordingly, feverfew may assist in migraine headache relief by inhibiting inflammation (e.g., via inhibiting release of inflammatory cytokines) and vasoconstriction/spasm thereby restoring normal blood flow.

Traditionally, feverfew has been administered as a raw leaf, either fresh or frozen, which is taken by chewing, by swallowing pills, tablets, capsules, by taking teas, or alcohol tinctures in which the feverfew is incorporated. It has also been administered as a tea with a concentration of 0.5-1 teaspoonfuls of feverfew per cup of boiling water. However, raw feverfew leaves are bitter and therefore unpleasant to chew and the tea is unpleasant to drink. Some evidence suggests that large amounts of feverfew cause oral ulcers or other irritations to the buccal membranes or mucosal membranes of the body including those of the mouth when taken at such high concentrations. In addition, the administration of feverfew by swallowing of the chewed material, drinking of tea, or swallowing of capsules, pills, or tinctures means that the feverfew must be released and dispersed to the central nervous system or other affected organs through the gastrointestinal system. Consequently, as discussed above, the active ingredients found in feverfew will not be readily available to a person to whom the herb has been administered. This has particularly significant drawback in the treatment of migraine headaches. In the present invention, feverfew is utilized in a powder form that has been milled or otherwise reduced in size to an average particle size of about 500 nm or less.

Ginger extract is derived from the ginger root, and may contain beneficial components in addition to gingerols, the generally recognized components of ginger extract. In the present invention, ginger is utilized in a powder form that has been milled or otherwise reduced in size to an average particle size of about 500 nm or less.

In a particularly preferred embodiment of the present invention, the compositions of the present invention are provided in combination with a mucosal permeation enhancer appropriate for enhancing the mucosal absorption of the composition employed (when, for example, a sublingual formulation is prepared). The mucosal permeation enhancer preferably comprises azone, sodium glycholate, sodium cholate, sodium taurocholate, sodium taurocholate plus EDTA, deoxycholate, sodium lauryl sulfate, lauric acid, ethanol, lysophosphatidyl choline, polysorbate, cyclodextrin, cetylpyridinium chloride, cetyltrimethylammonium bromide, benzalkonium chloride, sodium salicylate, sodium EDTA, aprotinin, dextran sulfate, linoleic acid, labrafil, transcutol, urea, methoxysalicylate, POE 23 lauryl ether, various surfactants and other mucosal permeation enhancers and combinations thereof. Most preferably, the mucosal permeation enhancer comprises polysorbate.

Method of Making

The present invention is also directed to a method of making a formulation, such as a spray formulation, with an average particle size for all active and therapeutic agents that is less than or equal to 500 nm. This particle size can be achieved by any suitable milling operation but preferably is achieved by utilizing a high-pressure, vacuum equipped high-shear mixer-granulator. The high-pressure, vacuum equipped high-shear mixer is made up of a vessel in which the mixture to be granulated is introduced that is equipped with a mixer and a mill that rotate with a normal mixer motion. Since the mixer and the mill have variable and adjustable speeds, they ensure densification and preparation of compositions in shorter times as compared to conventional mixers. These mixers are known in the art to reduce particle size. Any like mixer may be utilized for the methods detailed herein as long as particle size reduction is achieved. The drug-containing composition comprising feverfew, ginger and ibuprofen is blended to form a fine particulate. The blending process is carried out in a high pressure, vacuum equipped vessel having a high shear mixer/granulator mounted thereon. Subsequently, the resulting particulates found in the formulation (spray for example) will have a size equal to or less than 500 nm (nanometers).

The nonvolatile solvents can include, but are not limited to, the following: polyethylene glycol, propylene glycol, glycerin, vegetable oil, cotton seed oil, peanut oil, sesame oil, mineral oil, glycofurol, propylene glycol dicaprylate/dicaprate, glyceryl caprylate/caprate, oleic acid, polysorbates, sorbitan esters, caprylocaproyl macrogol-8 glycerides, ethoxydiglycol, and poloxamer block copolymers. Furthermore, cosolvency can be used to enhance the solubility of drugs in the mixed solvent system. In the preferred embodiment, the nonvolatile solvent is glycerin.

The emulsified fluid utilized in the high pressure, vacuum equipped vessel having a high shear mixer/granulator mounted thereon can be water or organic solvents such as, for instance, ethyl alcohol or other commonly used solvents, or mixtures of water and solvents.

The spray pharmaceutical composition also contains lecithin as the emulsifier. Egg or soy lecithin is suitable. Lecithin itself is a solid but is also available commercially as a liquid by having been mixed with oil such as soybean oil.

Sweeteners such as saccharin, aspartame (depending on the temperature used in preparation), sorbitol, corn syrup, etc. and other taste maskers such flavoring/masking agents including peppermint, orange, cherry, etc. can be included in the formulation. These agents can be added to any one or more of the components of the composition to insure their effectiveness throughout the composition.

Arginine is added as an agent to modify the pH of the spray pharmaceutical composition. The ideal pH of the final composition will be approximately 7.0-8.0. Additionally, arginine enhances the solubility and stability of ibuprofen within the final spray pharmaceutical composition.

The stable, water-soluble ibuprofen composition of the present invention has a solubility range of 0.0001% to 99.9999%. The process for forming the water-soluble ibuprofen begins by dissolving ibuprofen USP grade powder in a dissolution solution in succession manner according to the Homeopathic Pharmacopeia of the United States (HPUS), thereby forming a homeopathic premix. HPUS is a well-known manual that details homeopathic processing. One skilled in the art would know to use the manual as reference for producing homeopathic remedies, and is incorporated by reference.

The ibuprofen is dissolved using any necessary solvents, the type of which are detailed above. The dissolution solution contains water, alcohol, glycerin or a combination thereof. An example of the ibuprofen homeopathic premix is listed in Table 1. After forming the ibuprofen homeopathic premix, the mix is transferred to a high-pressure, vacuum equipped vessel having a high shear mixer mounted thereon. The ibuprofen homeopathic premix is mixed in the mixer for approximately 10-30 minutes, and preferably for approximately 15 minutes.

After mixing, the ibuprofen homeopathic premix is rested for approximately 10-20 minutes, preferably for approximately 15 minutes. This is followed by equilibrating the mixed ibuprofen homeopathic premix for approximately 24 hours. After equilibrating, the mixed ibuprofen homeopathic premix may be filtered through a filtration assembly, such as a sieve (10 micron sieve preferred). Through the mixing process, the particle size of the ibuprofen homeopathic premix will be reduced a size equal to or less than 500 nanometers (nm). Additionally, through the above detailed process, a stable, water-soluble ibuprofen composition having a solubility of 0.0001% to 99.9999% is formed.

The present invention is also directed to a process for preparing a sublingual spray pharmaceutical composition where the particle size of the composition is less than or equal to 500 nm. The process for forming the water-soluble ibuprofen begins by dissolving ibuprofen USP grade powder in a dissolution solution in succession manner according to the Homeopathic Pharmacopeia of the United States (HPUS), thereby forming a homeopathic premix. As detailed above, HPUS is a well-known manual that details homeopathic processing. The ibuprofen is dissolved using any necessary solvents, the type of which are detailed above. The dissolution solution contains water, alcohol, glycerin or a combination thereof.

The homeopathic premix is then transferred to a first container. After transferring, at least one homeopathic ingredient is added to the first container. The homeopathic ingredients include feverfew premix, ginger premix or a combination thereof. Preferably, a combination of feverfew and ginger is added to the homeopathic premix. Tables 2 shows the ingredients of the ginger premix, which involves dissolving ginger powder in a solvent solution including ethyl alcohol and water. This process is well-known and detailed in HPUS. Table 3 shows the ingredients of the feverfew premix, which involves dissolving feverfew powder in a solvent solution including ethyl alcohol and water. This process is well-known and detailed in HPUS.

This is followed by, in a second container, dissolving salt, sugar and at least one preservative in a solution of water, glycerin or a combination thereof. Lecithin (an emulsifier as detailed above), polysorbate or a combination thereof is added to the second container. This mixture is mixed in the high-pressure, vacuum equipped vessel having a high shear mixer mounted thereon under 5-20 psi and 2500-4000 RPM for approximately 5-15 minutes. Preferably, the high shear mixing will be done under 10-14 psi and 3500 RPM for approximately 10 minutes.

The mixed contents of the second container are then added to the first container containing the homeopathic premix with homeopathic ingredients. The mixture is the mixed in the high shear mixer for approximately 5-15 minutes and preferably for 10 minutes. After mixing, flavoring agents, as detailed above are added to the mixture along with arginine. After adding the flavoring agents and arginine, the mixture is mixed under the high shear mixer for approximately 5-15 minutes. After mixing, the mixture is rested for approximately 10-20 minutes, preferably for approximately 15 minutes. This is followed by equilibrating the mixture for approximately 24 hours. After equilibrating, the mixture is filtered through a filtration assembly, such as a sieve (10 micron sieve preferred). Through the mixing process, the particle size of the sublingual spray pharmaceutical composition will be reduced a size equal to or less than 500 nanometers (nm). The overall sublingual spray pharmaceutical composition is detailed in Table 4 based on a 100% w/w solution.

While the invention has been described in connection with what is presently considered to be the most practical and preferred embodiment, it is to be understood that the invention is not to be limited to the disclosed embodiments, but on the contrary, is intended to cover various modifications and equivalent arrangements included within the spirit and scope of the appended claims.

TABLE 1

| INGREDIENT | UNIT OF MEASURE | AMOUNT PER 20 LITERS |
|---|---|---|
| Ibuprofen powder | kg (kilograms) | 2 |
| Ethyl Alcohol | l (liters) | 10 |
| Glycerin | l (liters) | 7.600 |
| Water | l (liters) | 0.400 |

TABLE 2

| INGREDIENT | UNIT OF MEASURE | AMOUNT PER 4 LITERS |
|---|---|---|
| Ginger powder | g (grams) | 400 |
| Ethyl Alcohol | l (liters) | 2.6 |
| Water | l (liters) | 1.4 |

TABLE 3

| INGREDIENT | UNIT OF MEASURE | AMOUNT PER 4 LITERS |
|---|---|---|
| Feverfew powder | g (grams) | 400 |
| Ethyl Alcohol | l (liters) | 2.6 |
| Water | l (liters) | 1.4 |

TABLE 4

| INGREDIENTS | % w/w |
|---|---|
| Water | 46.2500 |
| Glycerin (99.5% USP) | 4.0000 |
| Salt (NaCl - 39.34% Na) | 0.3000 |
| Sucralose | 0.3500 |
| Lecithin | 3.0000 |
| Polysorbate | 0.6000 |
| Potassium Sorbate (granular) | 0.1500 |
| Ibuprofen (premix from Table 1) | 35.0000 |
| Ginger (premix from Table 2) | 0.3500 |
| Feverfew (premix from Table 3) | 3.5000 |
| Masking flavor | 2.0000 |
| Cherry flavor | 2.5000 |
| Arginine | 2.0000 |
| TOTAL | 100.0000 |

Method of Use

The invention provides methods and composition for administration, via sublingual, buccal, or the gastrointestinal tract. Sublingual administration offers advantages over other routes of administration. For example, compositions administered to the sublingual space have a rapid onset of action, reach high levels in the blood, avoid the first-pass effect of hepatic metabolism, and avoid exposure of the drug to fluids of the gastrointestinal tract. Additional advantages include easy access to the mucus membrane of the sublingual space so that an active substance contained in a therapeutic composition can be easily applied and localized. Further, there is good potential for prolonged delivery through the sublingual mucosal membrane.

The sublingual mucosa includes the membrane of the ventral surface of the tongue and the floor of the mouth. The sublingual mucosa is permeable, thus giving rapid absorption and acceptable bioavailability of many active substances. Furthermore, the sublingual mucosa is convenient, accessible, and generally well accepted. This route has been investigated clinically for the delivery of a substantial number of drugs.

Accordingly, in one aspect of the invention, the present spray formulation is designed for delivery to the sublingual mucosa, however, as detailed above, the composition may be administered via the buccal route and gastrointestinal tract. Spray administration containers for various types of sublingual sprays are known and typically will be suitable for the invention. The composition will commonly be contained in a small bottle or similar container with a focused nozzle from which the composition can be dispersed as a fine mist to be directed under the tongue. Using ambient air as the propelling agent, one can have the bottle made of a flexible plastic, so that merely squeezing the bottle's side propels the spray out through the nozzle into the sublingual space. Air is also the propelling agent for a pump sprayer, in which the user manipulates a small pump button which pumps air into the container and causes the liquid spray to be emitted on the return stroke. Alternatively, the bottle can be pressurized with a gas that is inert to the user and to the ingredients present in the composition. The gas will be dissolved under pressure in the container or may be generated by dissolution or reaction of a solid material that forms the gas as a product of dissolution or as a reaction product. Typical gases, which can be used, include nitrogen, argon, and a carbon dioxide.

Typically a subject will spray three to ten sprays at each administration of the sublingual spray pharmaceutical composition, with the administration being repeated on an as needed basis. During use a subject need merely raise their tongue and direct a spray comprising the formulation of the invention to the space under the tongue. The frequency of administration will be dependent on the nature of the usage. If administration is for relief of a current condition, such as a current headache, migraine, toothache, earache, and the like, initial relief effects can be expected within a few minutes of administration. Dosages may be repeated at intervals as the effect wears off, if the headache, migraine, toothache, or earache persists. The user will normally discontinue administration once the headache, toothache, or earache subsides. Administration can be resumed at a subsequent time when another headache, migraine, toothache, earache, or the like occurs.

In another aspect, the compositions of the invention may be administered at similar or smaller dosages and on a regular or less frequent basis to treat body aches or arthritic pain. The sublingual spray delivering system can be a unit dose delivery system. The volume of solution or suspension delivered per dose can be anywhere from 5 to 400 µl (microliters), typically between 50 to 250 µl. Delivery quantities of the spray pharmaceutical composition for sublingual use are typically about 200 µl per spray.

What is claimed is:

1. A process for preparing a stable, aqueous ibuprofen composition comprising the steps of:

mixing ibuprofen USP grade powder in a dissolution solution comprising a mixture of water, alcohol and glycerin to form a first ibuprofen mixture;

adding a homeopathic ingredient to said first ibuprofen mixture;

combining salt, sugar and at least one preservative in a solvent of water, glycerin or combination thereof, and mixing under high shear and under a vacuum of 10-14 psi to form a second mixture;

combining the resulting first ibuprofen mixture and second mixture to form a second ibuprofen mixture, and thereafter mixing under high shear under a vacuum of 10-14 psi to reduce the particle size of said second ibuprofen mixture to a particle size of 500 nanometers or less to form said stable aqueous ibuprofen composition.

2. The process according to claim 1, wherein said first ibuprofen mixture comprises two kilograms of ibuprofen USP grade powder and about 18 liters of said mixture of water, alcohol and glycerin.

3. The process according to claim 1, wherein said alcohol is ethyl alcohol.

4. The process according to claim 1, further comprising the step of filtering the stable aqueous ibuprofen composition through a filtration assembly.

5. The process according to claim 1, further comprising adding an herbal therapeutic agent to said first ibuprofen mixture and wherein said stable aqueous ibuprofen solution contains said herbal therapeutic agent having a particle size of about 0.01 to 500 nm.

6. A process for the preparation of a stable aqueous sublingual spray pharmaceutical composition, comprising the steps of:

mixing ibuprofen USP grade powder in a mixture comprising water, alcohol and glycerin to form a first ibuprofen mixture;

preparing a second mixture of a second active ingredient selected from the group consisting of feverfew, ginger and a combination thereof, and combining with said first mixture to produce a third mixture;

preparing a mixture of salt, sugar and a preservative in water and glycerin and mixing under vacuum of 10-14 psi and high shear and combining with said third mixture to produce a fourth ibuprofen mixture; and thereafter mixing said fourth mixture under vacuum of 10-14 psi and high shear to produce said stable aqueous sublingual spray wherein the particle size of said ibuprofen and second active ingredient in said stable sublingual spray pharmaceutical composition is 500 nanometers or less.

7. The process according to claim 6, wherein said mixture of salt, sugar and preservative in water and glycerin further comprises lecithin, polysorbate or a combination thereof.

8. The process according to claim 6, wherein said third mixture is mixed under said high shear for 5-15 minutes.

9. The process according to claim 6, further comprising the step of adding flavors, arginine or a combination thereof to said aqueous stable sublingual spray pharmaceutical composition and mixing under vacuum of 10-14 psi and high shear for about 5-15 minutes, and wherein said aqueous sublingual spray composition has a pH of about 7.0 to 8.0.

10. The process according to claim 6, further comprising the step of filtering the resulting sublingual spray pharmaceutical composition through a filtration assembly.

* * * * *